United States Patent [19]
Little

[11] 4,300,051
[45] Nov. 10, 1981

[54] TRAVELING CATHODE X-RAY SOURCE
[75] Inventor: Roger G. Little, Bedford, Mass.
[73] Assignee: Spire Corporation, Bedford, Mass.
[21] Appl. No.: 113,811
[22] Filed: Jan. 21, 1980

Related U.S. Application Data

[63] Continuation of Ser. No. 920,192, Jun. 29, 1978, abandoned.

[51] Int. Cl.³ .............................................. G03B 41/16
[52] U.S. Cl. ................................. 250/445 T; 250/406; 313/60
[58] Field of Search ............... 250/445 T, 406; 313/60

[56] References Cited
U.S. PATENT DOCUMENTS

| | | | |
|---|---|---|---|
| 4,075,489 | 2/1978 | Neal | 250/445 T |
| 4,128,781 | 12/1978 | Flisikowski | 313/60 |
| 4,227,088 | 10/1980 | Maydan | 250/445 T |

Primary Examiner—Craig E. Church
Attorney, Agent, or Firm—Morse, Altman, Oates & Dacey

[57] ABSTRACT

A scanning X-ray source with an evacuated cylindrical chamber which bounds a cavity that is configured to receive a patient undergoing diagnosis. A moving electron beam is generated from a cathode which is attached to a rotating drum that is mounted within the chamber. The moving electron beam is directed towards and moves along a fixed annular anode mounted within the chamber. The points of beam impingement on the anode define a moving source of X-rays which sequentially irradiate the body from all directions. A plurality of detectors mounted adjacent the anode measure the amount of X-ray absorption. A processor receives the detected signals and reconstructs the absorption at each point to provide a two-dimensional density presentation for each body cross section.

8 Claims, 3 Drawing Figures

TRAVELING CATHODE X-RAY SOURCE

This is a continuation of application Ser. No. 920,192, filed on June 29, 1978, now abandoned.

BACKGROUND OF THE INVENTION

1. Field of Invention

The present invention relates to X-ray equipment and, more particularly, is directed towards a moving source of X-rays.

2. Description of the Prior Art

X-rays computed tomography for medical diagnostic processes involves the use of a moving source of X-rays for producing either a single cross-sectional density profile of an irradiated subject under diagnosis or a two-dimensional density profile from a spatially separated sequence of such cross-sectional profiles. Since it is necessary to irradiate the subject from a large number of different directions in a common cross-sectional plane, the X-ray source encircles or scans the subject for at least one half an orbit and, in many instances, for an entire orbit.

Prior art approaches for moving the X-ray source involve the direct mechanical transport of a standard hard vacuum X-ray generating tube and its associated high voltage power cables. In order to eliminate blurring of the density profile due to subject motion, such as respiration and heart beat, it is necessary that the total scan time is made to be substantially less than the time intervals characteristic of such subject motions. Due to the difficulties associated with faster mechanical transport of the X-ray tube, and such associated problems as coiling and uncoiling of high voltage cables, attempts at increased scan rates have been met with qualified acceptance. Systems of the type shown in U.S. Pat. No. 3,106,640, which provide a moving source of X-rays by deflecting a rotating beam onto a circular target, have been introduced with varying degrees of success.

SUMMARY OF THE INVENTION

An object of the present invention is to provide a moving source of X-rays which does not suffer from the limitations heretofore discussed.

Another object of the present invention is to provide an X-ray system for presenting a two dimensional absorption density profile of an irradiated subject under diagnosis.

A further object of the invention is to provide an X-ray system having a moving source of X-rays for irradiating a subject under diagnosis from all directions. According to the invention, the subject is positioned within a cavity that is bounded by an evacuated cylindrical chamber, the subject being placed along the centerline of the chamber. A rotating drum is mounted concentrically within the chamber and carries a cathode. A fixed annular anode is located within the chamber adjacent the cathode. An electron beam emitted from the cathode impinges upon and travels along the anode as the drum rotates. X-rays are generated at the points of beam impingement on the anode. The points of beam impingement define a moving source of X-rays which emanate sequentially from the anode and irradiate the subject from all directions. A plurality of X-ray detectors at selected locations adjacent the anode measure the amount of X-ray absorption. The detected signals are processed by a computer which reconstructs the absorption at each point in the subject to provide a two-dimensional density presentation for each subject cross section.

Other objects of the present invention will in part be obvious and will in part appear hereinafter.

The invention accordingly comprises the apparatuses and systems, together with their parts, elements and interrelationships that are exemplified in the following disclosure, the scope of which will be indicated in the appended claims.

BRIEF DESCRIPTION OF THE DRAWINGS

A fuller understanding of the nature and objects of the present invention will become apparent upon consideration of the following detailed description taken in connection with the accompanying drawings, wherein.

DETAILED DESCRIPTION OF THE PREFERRED EMBODIMENTS

Figure 1:
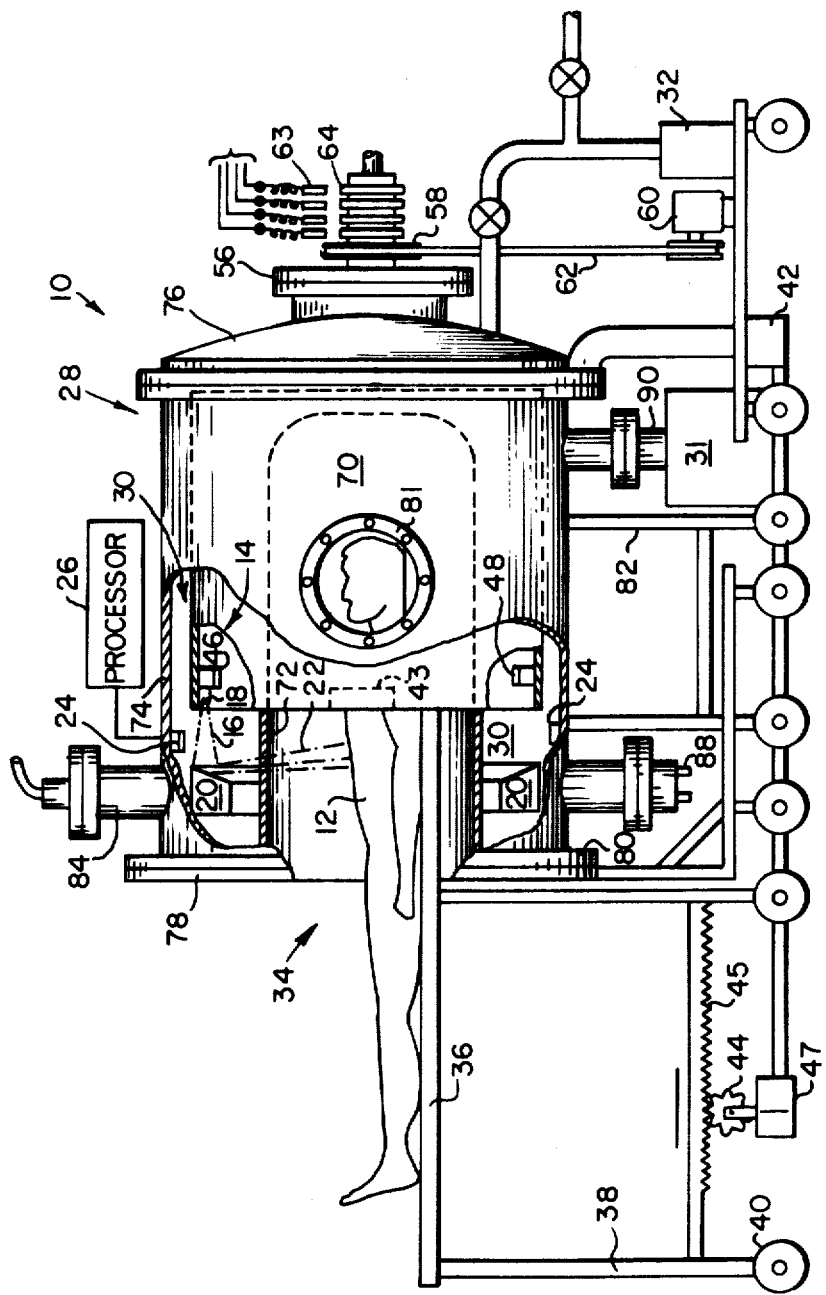
FIG. 1 is a side elevation, partly broken away, of an X-ray system embodying the invention.

Referring now to the drawings, particularly FIG. 1, there is shown an X-ray system 10 embodying the present invention for providing a two-dimensional density presentation for each body cross section of a subject 12 under diagnosis. X-ray system 10 includes a traveling cathode X-ray source 14 in which an electron beam 16 emitted from a cathode 18 rapidly travels along a fixed annular anode 20. X-rays 22 are generated at the point of beam impingement on anode 20, the points of beam impingement along the anode structure defining a moving source of X-rays. The X-rays emanate sequentially from anode 20 and irradiate subject 12 from all directions. A scan time of one thirtieth of a second permits heart studies and effectively eliminates motion effects of the heart on the image. A plurality of X-ray detectors 24 positioned adjacent anode 20 measure the amount of X-ray absorption in each direction. The detected signals are applied to a processor 26 which reconstructs the absorption at each point and generates data signals defining a two-dimensional density presentation for each body cross section. U.S. Pat. application of Stein et al., Ser. No. 726,556, filed Sept. 27, 1976 for Tomography Scanning With Radiant Energy Source And Detectors Relatively Displaced, describes the use of a plurality of detectors and the processing of signals for this purpose, which application and its teachings are herewith incorporated herein by reference.

X-ray source 14 includes a reentrant housing 28 having a cylindrical chamber 30 which is evacuated by an ion pump 31 and a mechanical vacuum pump 32. Pump 32 is provided for rough pumping during start-up and ion pump 31 is provided for reducing the pressure in chamber 30 to approximately $1 \times 10^{-6}$ torr. Chamber 30 bounds a reentrant cavity 34 which is configured to receive subject 12 on a bed 36, the subject being positioned at the center line of the chamber. Bed 36 is mounted on a frame 38 that is supported on wheels 40. A drive motor 42 is operatively connected to a pinion gear 44 which engages a rack 45 via a clutch mechanism 47 for moving bed 36 in and out of cavity 34. Drive motor 42 is energized to move bed 36 horizontally in short increments in the order of 0.1 inch after each rotational X-ray scan. It is to be understood that bed 36 is adjustable vertically and transversely so that the area of subject 12 under diagnosis is centered in the rotating X-ray beam.

A rotating drum 46, preferably composed of a high temperature strength aluminum alloy, is mounted concentrically within chamber 30 and carries cathode 18. A spare cathode 48 is mounted to drum 46 diametrically opposite cathode 18. Optionally, weights 43 are attached to drum 46 for balance. In alternate embodiments, the number of active cathodes is other than one, for example, two, three, four or more. The multiple cathodes are spaced equidistant from each other about the axis of rotation of drum 46. Simultaneous use of multiple cathodes permits collection of a complete set of data with good photon statistics and lower rotation rate for the cathode assembly without increasing the total scan time. That is, the use of two or three cathodes results in drum 46 rotation speeds of 900 RPM and 600 RPM respectively, rather than 1800 RPM for a single cathode. Each of the multiple cathodes can be operated at substantially the same emission current as a single cathode, thereby providing more total X-ray flux.

Figure 2:
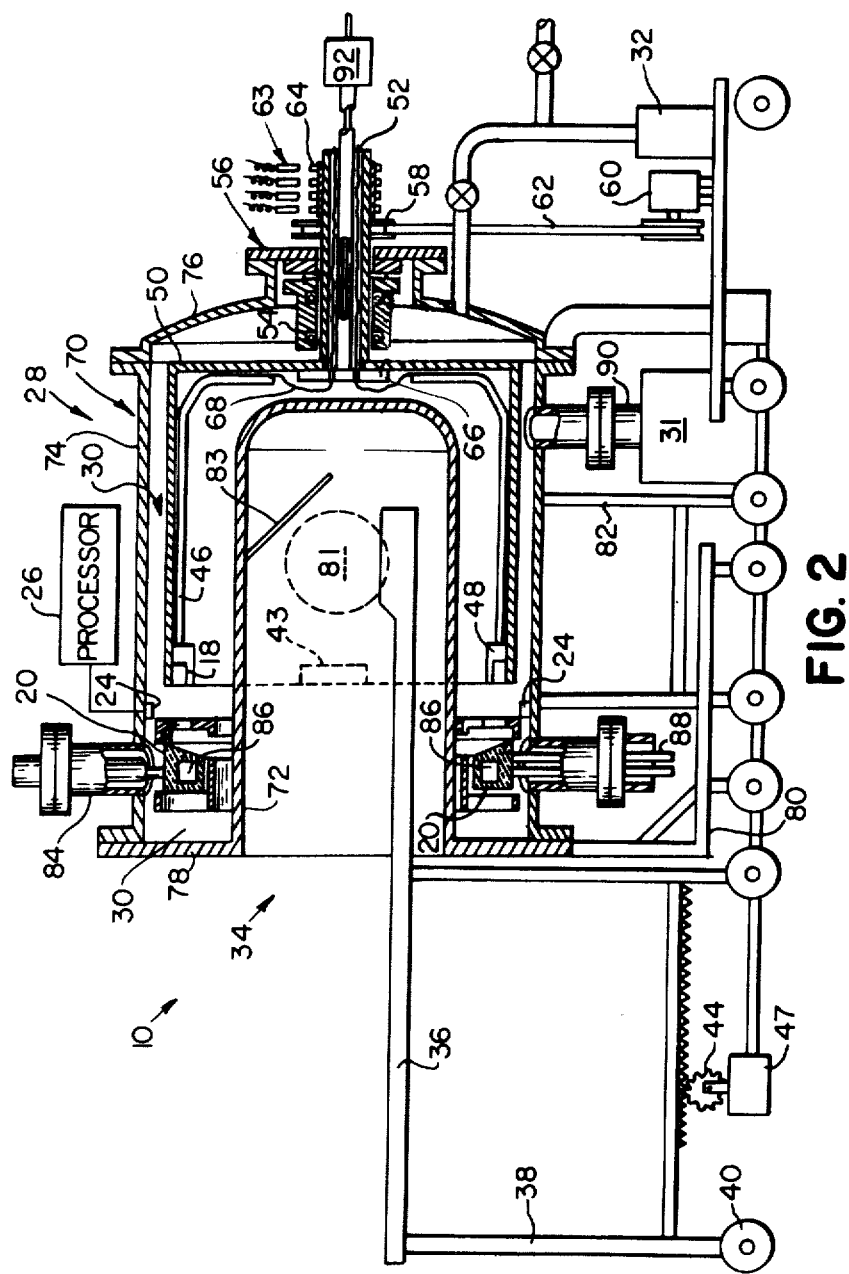
FIG. 2 is a side elevation, partly in section, of the system of FIG. 1 showing certain details thereof.

As best shown in FIG. 2, the end of drum 46 to which cathodes 18 and 48 are attached is opened and the other end of the drum is closed by an end plate 50 which is mounted on a hollow drive shaft 52. End plate 50 is a circular plate which constitutes a fly wheel that is operative to keep the rotational speed of drum 46 constant. Drive shaft 52 is supported by ball bearings 54 that are part of a rotary motion vacuum feedthrough 56. One end of drive shaft 52 enters vacuum chamber 30 via feedthrough 56 and is connected to end plate 50, the opposite end of the drive shaft is outside of the vacuum chamber and under atmospheric pressure. A pulley wheel 58 that is captively held to shaft 52, is drivingly connected to a motor 60 by an endless belt 62. Preferably, belt 62 is a cog type belt to avoid slippage at pulley 58. A power supply (not shown) is connected to cathode 18 via brushes 63, slip rings 64, a conduction rod and feedthrough flange assembly 66 and conductors 68. Electron beam 16 is directed towards fixed annular anode 20 which is mounted within chamber 30. X-rays are generated as a result of the impingement of high energy electrons on anode 20.

Housing 28, preferably composed of stainless steel, includes a cylindrical portion 70 having an inner wall 72 and an outer wall 74 which bound chamber 30. A semispherical header 76 closes one end of cylindrical portion 70 and an annular flange 78 closes the opposite end of the cylindrical portion to form sealed chamber 30. When flange 78 is unbolted, inner wall 72 may be moved horizontally on a wheeled dolly 80 to provide access to rotating drum 46, cathodes 18, 48, and anode 20. Outer wall 74 is mounted on a wheeled dolly 82 to provide separation of header 76 from cylindrical portion 70. Cylindrical portion 70 is provided with diametrically opposed windows 81 that permit subject 12 to see through chamber 30 and allow viewing of the subject. An inclined mirror 83 mounted over the head of subject 12 is provided for axial viewing of and by the patient.

Anode 20 is supported primarily by a cable receptacle 84 used as a high voltage feedthrough. Typically, the high voltage applied to anode 20 is approximately 150 kV. Anode 20 is a fluid cooled ring composed of tungsten and having an inner chamber 86 through which a coolant flows. A dielectric cooling fluid is carried to anode 20 via coolant lines 88 which also provide partial support for the anode. Ion pump 21, for example a 500 l/sec ion pump, is connected to a port 90 which is mounted to outer wall 74. In the illustrated embodiment, by way of example, the slope of the face of fluid cooled anode 20 towards which the electron beam is directed is approximately 14° and electron beam 16 is rectangular, 0.2 cm wide by 0.8 cm long in the radial direction. The area of the focal spot as viewed from the center of anode 20 is approximately 0.2 cm by 0.2 cm square. The focal spot travels along anode 20 at such a rate that one revolution is completed in one-thirtieth of a second. A positive grid pulse generated from a grid supply (not shown) is applied to cathode 18, for example a cathode having two spiral wound filaments that are composed of a metal such as pure tungsten, to turn on electron beam 16. Preferably, a filament booster circuit (not shown) is energized to increase cathode 16 temperature and emission prior to application of the grid pulse. Each emission pulse has a duration of one thirtieth of a second as electron beam 16 makes one complete revolution. Heat dissipated by cathode 18 is removed by water cooling of rod and feedthrough flange assembly 66, such cooling being provided through a rotary water union 92.

Figure 3:
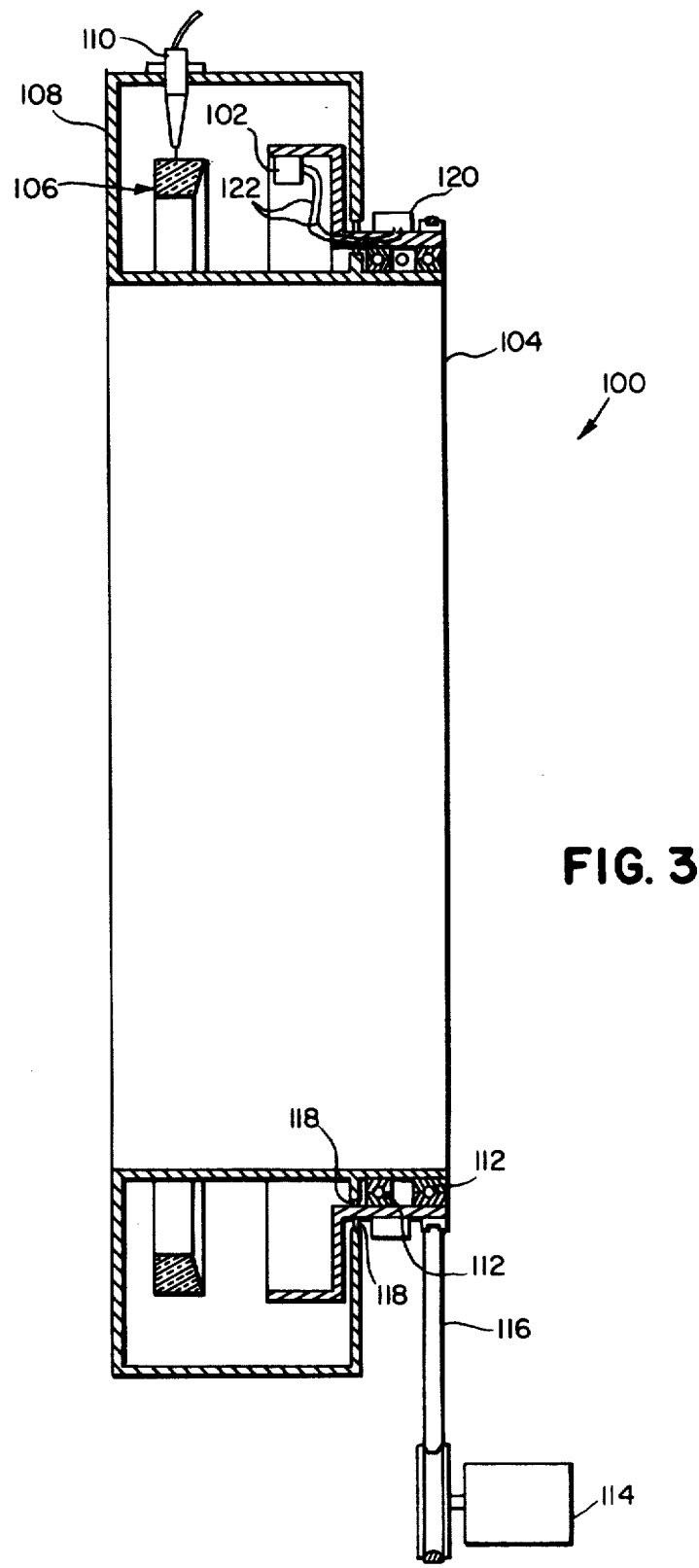
FIG. 3 is a side elevation, partly in section, of an alternate embodiment of an x-ray system constructed in accordance with the invention.

Referring now to the alternate embodiment of the invention depicted in FIG. 3, there is shown a traveling cathode X-ray source 100 with a cathode 102 that is mounted to a drum 104 which is opened at both ends. The drum 104 is rotatably mounted within a stationary housing 108 having an open annulus configuration and defining a toroidal shape vacuum envelope. An annular anode 106 is mounted within the stationary housing 108. Anode 106 is carried by a high voltage feedthrough assembly 110 which is mounted to housing 108. Drum 104 is supported on bearings 112 and is rotated by a motor 114 which is drivingly connected to the drum via an endless belt 116. Vacuum seals 118 are provided between drum 104 and housing 108. A power source (not shown) is connected to cathode 102 via slip rings 120 and conductors 122. The structure and function of anode 106 and cathode 102 are similar to anode 20 and cathode 18, respectively. The operation of traveling cathode X-ray source 100 and generation of a moving source of X-rays correspond to the description of FIGS. 1 and 2.

The traveling cathode X-ray system of the invention provides a moving source of X-rays which sequentially irradiate a subject under diagnosis from all directions for presentation of a two-dimensional density profile of each body cross section. Motion studies of the heart throughout a cardiac cycle are within the capabilities of the system. A continuous succession of rapid (1/30 second nominal) scans provider a series of cross-sectional images of the heart, with typically 15 to 30 of such temporal segments completing an entire cardiac cycle. The individual images are displayed in rapid and repeated succession to provide a motion picture type presentation of the heart throughout a cardiac cycle.

Since certain changes may be made in the above description without departing from the scope of the invention herein involved, it is intended that all matter contained in the foregoing disclosure be construed in an illustrative and not in a limiting sense.

What is claimed is:
1. An X-ray apparatus comprising:
   (a) means defining a region in which a subject to be irradiated may be positioned;

(b) a closed evacuated chamber surrounding said region;
(c) electron beam generating means within said evacuated chamber, said beam generating means including cathode means mounted for orbital movement within said chamber along a first circular path about said region; and
(d) cooperating anode means fixed in position within said evacuated chamber along a second circular path adjacent to and coaxial with said first circular path, said cathode means and said anode means disposed about a subject positioned in said region, said anode means being constructed to emit X-rays from said evacuated chamber into said region from the point of impingement on said anode means of beamed electrons emitted by said cathode means, the point of emission of said X-rays from said fixed anode means into said region moving along said second circular path as said cathode means moves along said first circular path thereby to irradiate said subject from successively different directions;
(e) said means defining said region and said closed evacuated chamber surrounding said region comprising a housing having an open annulus configuration and defining a toroidal shape vacuum envelope.

2. An X-ray apparatus comprising:
(a) means defining a region in which a subject to be irradiated may be positioned;
(b) a closed evacuated chamber surrounding said region;
(c) electron beam generating means within said evacuated chamber, said beam generating means including cathode means mounted for orbital movement within said chamber along a first circular path about said region, said cathode means comprising a plurality of cathodes equidistantly mounted from each other along said first path;
(d) cooperating anode means fixed in position within said evacuated chamber along a second circular path adjacent to and coaxial with said first circular path, said cathode means and said anode means disposed about a subject positioned in said region, said anode means being constructed to emit X-rays from said evacuated chamber into said region from the point of impingement on said anode means of beamed electrons emitted by said cathode means, the point of emission of said X-rays from said fixed anode means into said region moving along said second circular path as said cathode means moves along said first circular path thereby to irradiate said subject from successively different directions said anode means at said point of impingement thereon of said beamed electrons being sloped at a slight angle toward said cathode means of about 14 from a plane normal to the axis of rotation of said cathode means; and
(e) means for supporting said subject to be irradiated within said region, said means being axially movable in said region in small increments following each orbital movement of said cathode means, one orbital movement of said cathode means defining one scan and said one scan being effected in a scan time of about one thirtieth of one second;
(f) said closed evacuated chamber evacuated first by a mechanical vacuum pump and then by an ion pump to a pressure of about $1 \times 10^{-6}$ torr.

3. The X-ray apparatus of claim 2 including a plurality of weights also mounted for orbital movement within said chamber along said first circular path.

4. A moving source of X-Rays comprising:
(a) a reentrant housing formed with a cylindrical chamber that bounds a cavity configured to receive a subject under diagnosis;
(b) fixed annular anode means mounted within said chamber concentrically about a longitudinal axis of said chamber;
(c) rotatable support means mounted within said housing concentrically about said longitudinal axis, at least a portion of said support means defining a surface of revolution about said longitudinal axis of said chamber and about said subject under diagnosis;
(d) cathode means mounted to said portion of said support means defining said surface of revolution, said cathode means disposed within said chamber adjacent said anode means, said cathode means orbiting in a circular path defined by said surface of revolution about said longitudinal axis of said chamber and about said subject under diagnosis when said support means rotates, said cathode means having energized and deenergized states, an electron beam emitted from said cathode means when in said energized state;
(e) means for directing said electron beam towards said anode means for impingement thereon, said electron beam traveling along said anode means as said cathode means travels in said circular path, X-rays generated at the points of said electron beam impingement on said anode means, said points of impingement defining a moving source of X-rays as said electron beam travels along said anode means;
(f) detector means mounted within said chamber adjacent said anode means, said X-rays generated by said anode means directed towards said subject and towards said detector means, and means coupled to said detector means for measuring the amount of X-ray absorption by said subject; and
(g) pulse means for energizing said cathode means, said pulse means generating a pulsed signal for energizing said cathode means for a period corresponding to one revolution of said rotatable support means.

5. The moving source of X-rays as claimed in claim 1 wherein said support means is a drum, said cathode means mounted at an opened end of said drum, an annular plate defining a fly wheel mounted to an opposite end of said drum, said fly wheel operative to maintain the rotational speed of said drum constant.

6. An X-ray system comprising:
(a) reentrant housing formed with a cylindrical chamber that bounds a reentrant cavity configured to receive a subject under diagnosis;
(b) vacuum means connected to said housing for evacuating said chamber;
(c) drum means rotatably mounted within said chamber, said drum means concentrically disposed about a longitudinal axis of said chamber, a portion of said drum means defining a surface of revolution about said longitudinal axis and about said subject under diagnosis;
(d) drive means operatively connected to said drum means, said portion of said drum means defining said surface of revolution traveling in a circular path about said longitudinal axis as drum means is rotated by said drive means;

(e) fixed annular anode means mounted within said chamber, said anode means disposed concentrically about said longitudinal axis of said chamber and about said subject under diagnosis;

(f) cathode means mounted to said portion of said drum means, said cathode means disposed adjacent said anode means, said cathode means orbiting in said circular path about said longitudinal axis and about said subject under diagnosis when said drum means is rotated;

(g) means connected to said cathode means for energizing said cathode means, an electron beam emitted from said cathode means when energized;

(h) means for directing said electron beam towards said anode means, said electron beam traveling along and impinging upon said anode means as said drum means rotates, X-rays generated at the points of said electron beam impingement defining a moving source of X-rays as said electron beam travels along said anode means, said X-rays directed towards said subject and irradiating said subject from all directions as said electron beam travels along said anode means;

(i) detector means mounted within said chamber in a path of said X-rays for detecting said X-rays passing through said subject;

(j) said means for energizing said cathode means includes pulse means for generating pulsed signals which are applied to said cathode means, each said pulsed signal operative to energize said cathode means for a period corresponding to one revolution of said drum means.

7. The X-ray system as claimed in claim 6 wherein said drum means is an open ended cylinder, said cathode means mounted at said opened end of said cylinder, an annular plate mounted to said cylinder and closing the other end of said cylinder, said plate constituting a fly wheel for maintaining the rotational speed of said drum means constant.

8. The X-ray system as claimed in claim 7 including a movable bed configured to support said subject and means for moving said bed in and out of said reentrant cavity, portions of said subject under diagnosis positioned along said longitudinal axis of chamber when supported on said bed within said reentrant cavity.

* * * * *